United States Patent [19]

Trinh et al.

[11] Patent Number: 6,001,789
[45] Date of Patent: Dec. 14, 1999

[54] TOILET BOWL DETERGENT SYSTEM CONTAINING BLOOMING PERFUME

[75] Inventors: Toan Trinh, Maineville; Dennis Ray Bacon, Milford; Alex Haejoon Chung, West Chester; Ricky Ah-Man Woo, Hamilton; Patricia Ann Blondin, Fairfield, all of Ohio

[73] Assignee: The Procter & Gamble Company, Cincinnati, Ohio

[21] Appl. No.: 09/025,716

[22] Filed: Feb. 18, 1998

Related U.S. Application Data

[63] Continuation-in-part of application No. 08/618,634, Mar. 19, 1996, abandoned.

[51] Int. Cl.$^6$ .................. C11D 3/50; C11D 1/62; C11D 1/90
[52] U.S. Cl. .......... 510/191; 510/192; 510/193; 510/471; 510/490; 510/447; 510/451; 510/101; 510/102; 510/103; 510/104; 510/106
[58] Field of Search ................ 510/191, 192, 510/193, 471, 490, 447, 101, 102, 103, 104, 106, 451

[56] References Cited

U.S. PATENT DOCUMENTS

| | | | |
|---|---|---|---|
| 4,043,931 | 8/1977 | Jeffrey et al. | 252/93 |
| 4,149,986 | 4/1979 | Dickson | 252/108 |
| 4,187,251 | 2/1980 | Schleppnik | 260/586 |
| 4,229,410 | 10/1980 | Kosti | 422/28 |
| 4,252,785 | 2/1981 | Isoldi | 424/19 |
| 4,267,067 | 5/1981 | Sprecker et al. | 252/174.11 |
| 4,269,723 | 5/1981 | Barford et al. | 252/106 |
| 4,396,522 | 8/1983 | Callicott et al. | 252/163 |
| 4,438,015 | 3/1984 | Huber | 252/174.24 |
| 4,460,490 | 7/1984 | Barford et al. | 252/92 |
| 4,476,046 | 10/1984 | Wong et al. | 252/550 |
| 4,491,988 | 1/1985 | Mizuno | 4/228 |
| 4,515,705 | 5/1985 | Moeddel | 252/174.12 |
| 4,534,071 | 8/1985 | Russomanno | 4/228 |
| 4,654,341 | 3/1987 | Nelson et al. | 514/241 |
| 4,722,801 | 2/1988 | Bunczk et al. | 252/106 |
| 4,722,802 | 2/1988 | Hutchings et al. | 252/174 |
| 4,738,728 | 4/1988 | Barford et al. | 134/34 |
| 4,813,084 | 3/1989 | Buecheler et al. | 4/231 |
| 4,820,449 | 4/1989 | Menke et al. | 252/544 |
| 4,874,536 | 10/1989 | Strickland, Jr. et al. | 252/90 |
| 4,899,398 | 2/1990 | Hutchings et al. | 4/228 |
| 4,911,858 | 3/1990 | Bunczk et al. | 252/106 |
| 4,911,859 | 3/1990 | Bunczk et al. | 252/106 |
| 4,952,559 | 8/1990 | Login et al. | 512/10 |
| 4,994,266 | 2/1991 | Wells | 424/76.7 |
| 4,998,300 | 3/1991 | Sharifzadeh | 4/420.4 |
| 5,043,090 | 8/1991 | Camp et al. | 252/106 |
| 5,061,393 | 10/1991 | Linares et al. | 252/143 |
| 5,066,419 | 11/1991 | Walley et al. | 252/174.11 |
| 5,089,162 | 2/1992 | Rapisarda et al. | 252/102 |
| 5,110,492 | 5/1992 | Casey | 252/90 |
| 5,139,687 | 8/1992 | Borgher, Sr. et al. | 252/8.6 |
| 5,154,842 | 10/1992 | Walley et al. | 252/8.6 |
| 5,188,753 | 2/1993 | Schmidt et al. | 252/132 |
| 5,190,915 | 3/1993 | Behan et al. | 512/2 |
| 5,232,613 | 8/1993 | Bacon et al. | 252/8.6 |
| 5,232,632 | 8/1993 | Woo et al. | 252/546 |
| 5,234,610 | 8/1993 | Gardlik et al. | 252/8.6 |
| 5,246,611 | 9/1993 | Trinh | 252/8.6 |
| 5,256,328 | 10/1993 | Cavanagh et al. | 252/102 |
| 5,336,665 | 8/1994 | Garner-Gray et al. | 512/4 |
| 5,342,550 | 8/1994 | Burke et al. | 252/548 |
| 5,384,186 | 1/1995 | Trinh | 428/240 |
| 5,404,594 | 4/1995 | Ring et al. | 4/224 |
| 5,500,137 | 3/1996 | Bacon et al. | 252/8.6 |
| 5,500,138 | 3/1996 | Bacon et al. | 252/8.8 |
| 5,536,451 | 7/1996 | Masters et al. | 510/405 |
| 5,543,439 | 8/1996 | McDermott et al. | 523/102 |
| 5,554,588 | 9/1996 | Behan et al. | 512/1 |
| 5,562,850 | 10/1996 | Woo et al. | 510/151 |
| 5,676,163 | 10/1997 | Behan et al. | 131/213 |
| 5,723,420 | 3/1998 | Wei et al. | 510/101 |
| 5,759,974 | 6/1998 | Menke et al. | 510/191 |

FOREIGN PATENT DOCUMENTS

| | | | |
|---|---|---|---|
| 0 167 085 A2 | 7/1984 | European Pat. Off. | C11D 17/00 |
| WO 94/19449 | 2/1993 | WIPO | C11D 17/00 |
| WO 94/28107 | 12/1994 | WIPO | C11D 3/50 |
| WO 96/04362 | 2/1996 | WIPO | C11D 17/00 |

OTHER PUBLICATIONS

"A Quantitative Study of Factors that Influence the Substantivity of Fragrance Chemicals on Laundered and Dried Fabrics", Escher et al., JAOCS, vol. 71, No. 1 (Jan. 1994) (previously submitted in prior application).
"What Makes a Fragrance Substantive", Muller et al., Givaudan–Roure Research Ltd., CH–6800, Dubendorf Switzerland (previously submitted in prior application).

*Primary Examiner*—Mark Kopec
*Assistant Examiner*—Charles Boyer
*Attorney, Agent, or Firm*—Robert B. Aylor; Jason J. Camp

[57] ABSTRACT

Toilet bowl detergent compositions, preferably blocks of the "in-tank" or "rim-block" types, contain from about 0.1% to about 10% of a blooming perfume composition comprising blooming perfume ingredients selected from the group consisting of: ingredients having a boiling point of less than about 260° C. and a ClogP of at least about 3, and wherein said perfume composition comprises at least 5 different blooming perfume ingredients, a cleaning system comprising: detergent surfactant preferably of the amphoteric type, more preferably zwitterionic, even more preferably one that contains a carboxylate group and a cationic group, and even more preferably a fatty acid amidoalkylene betaine, and detergent builder, preferably polycarboxylate chelating agent, more preferably, citric acid, or similar polycarboxylic acid, are combined with some means of creating the desired concentration of the cleaning system in the toilet bowl water, preferably by means of blocks with a dissolution retarding system, preferably with the dissolution retarding system comprising a combination of water soluble cellulosic polymer, more preferably hydroxyethyl cellulose or hydroxypropyl cellulose and, polyethylene glycol containing polymer, any perfume present optionally being contained in a protective carrier. The compositions have a pH, in use, of from about 2 to about 11 and the blocks are preferably extremely homogeneous.

18 Claims, No Drawings

TOILET BOWL DETERGENT SYSTEM CONTAINING BLOOMING PERFUME

REFERENCE TO RELATED APPLICATIONS

This is a continuation-in-part of U.S. Ser. No. 08/618,634, filed Mar. 19, 1996 abandoned.

FIELD OF THE INVENTION

This invention relates to toilet bowl cleaners, especially those of the block type that typically either sit, or hang, in the water reservoir ("tank"), or hang on the rim of a toilet bowl and rely upon the water from the "flush" to dissolve a portion of the block and wash the ingredients into the pooled water in the bowl. There is a continuing need for improved compositions of this type.

BACKGROUND OF THE INVENTION

Solid delivery systems provide effective and convenient treatment of the toilet bowl water through the use of slow dissolving blocks containing the desired cleaning ingredients. Solid blocks are extremely cost effective and typically contain materials to control dissolution. A variety of approaches have been used to control the release. The actives can be selected to have the desired limited solubility as in U.S. Pat. No. 4,820,449, Menke et al. or the actives can be incorporated into a microporous resin, as in U.S. Pat. No. 4,252,785, Isoldi.

Long-chain cellulosic polymers have been used as a major solid component to control dissolution and release of the active ingredients into the pooled water. For example, Barford et al., U.S. Pat. No. 4,269,723 teaches the use of water soluble, water dispersible clays and cellulosics to retard dissolution. Barford makes mention of chemically modified celluloses such as ethyl cellulose, methyl cellulose, sodium carboxymethyl cellulose, ethyl hydroxyethyl cellulose, and the like. Barford, et al., discloses a process for making lavatory cleansing blocks by tableting a free flowing particulate mix consisting essentially of, on a weight basis, from 5 to 90% of a surface active component and from 0.5 to 75% of one or more binders selected from clays and water soluble or water dispersible gel forming organic polymeric materials. Various optional components are also mentioned by Barford; namely, dyestuffs, perfume, water soluble fillers, water softening or chelating agents, solid water soluble acids, inert water insoluble inorganic or organic fillers, tablet lubricants, and agents having disinfecting or germicidal activity.

U.S. Pat. No. 4,460,490 to Barford, et al., discloses a free standing lavatory cleansing block that comprises a shaped body formed of a slow dissolving cleaning composition containing a surface active agent and a tablet comprising a bleaching agent embedded in or adhered to the shaped body. The shaped body, according to the '490 patent, may be melt cast, tableted, or extruded, depending upon the geometry of the shaped body. The shaped body preferably comprises the aforesaid surface active agent and a solubility control agent, for example, a water soluble or water dispersible gel forming polymer, for example, chemically modified celluloses.

Ziek et al., U.S. Pat. No. 4,722,802, also discloses hydrated cellulosics to retard dissolution. In Ziek et al., the advantages of curing the resultant block are also discussed. Similarly, Bunczak et al., U.S. Pat. Nos. 4,911,858 and 4,911,859, disclosed very high molecular weight polyethylene oxide polymers together with guar gum and calcium salt to form a gelatin matrix that slows dissolution of the solid system.

Like Menke et al., U.S. Pat. No. 4,820,449, Jeffrey et al., U.S. Pat. No. 4,043,931, seeks slow dissolution through the use of mono- or di-alkanolamides of various aliphatic chain lengths while adding ethylene oxide/propylene oxide block copolymer surfactants with unspecified monomer ratios. Jeffrey, et al., discloses a lavatory cleansing block comprising a solid carrier base which is a mixture of two or more nonionic surface active agents, one of which is relatively insoluble in water and the other of which is relatively soluble in water. The lavatory block of Jeffrey may optionally include perfume, dyestuff, germicide, and fillers, the latter being for example, a water softener such as a alkali metal polyphosphate. The blocks of Jeffrey are made by tableting.

Polyethylene glycol, having a molecular weight of about 8000, is taught in U.S. Pat. No. 5,342,550, Burke et al. together with one or more fillers or binding agents for use in solid block compositions. Examples of acceptable binding agents disclosed include the water-soluble alkali metal and alkaline earth metal salts. The compositions also preferably comprise one or more additional ingredients such as, for example, cleaning agents, deodorizers or perfumes, bactericides, bacteriostats, hard water film inhibitors, stain inhibitors and dyes.

U.S. Pat. No. 4,438,015 to Huber discloses lavatory cleansing blocks comprising as a solid carrier base a mixture comprising a major proportion of a nonionic surface active compound and a minor proportion of a partially esterified copolymer of vinylmethyl ether and maleic anhydride (PVM/MA). The blocks of Huber are melt cast.

U.S. Pat. No. 4,229,410 to Kosti discloses a bacteriostatic toilet element comprising a water sensitive, water soluble or swellable binding agent and a bacteriostatic and/or deodorizing and/or coloring agent. Kosti's element may be melt cast or extruded.

As discussed above, surfactant cleansing blocks can be made by tablet forming methods, casting or extrusion as described for instance in U.S. Pat. Nos. 4,043,931; 4,269,723; 4,460,490; 4,438,015; 4,722,802; 4,738,728; and 4,082,449. The surfactant in these cleansing blocks is released gradually over an extended period of time to clean the porcelain surface of the toilets.

Toilet bowl detergent compositions that are not blocks can also be used to form detergent solutions. There are a variety of dispensers that provide for controlled release. For example, U.S. Pat. No. 4,813.084, Buecheler et al., discloses a rim-block holder that can use granular compositions. Similarly, there are a multitude of "passive" dispensers, such as U.S. Pat. No. 4,462,121, Dirksing et al., that can use liquid or solid compositions to form the cleaning solution in the toilet tank.

All of the above patents are incorporated herein by reference.

SUMMARY OF THE INVENTION

The present invention comprises a block detergent composition for keeping a toilet bowl clean comprising:

(1) from about 0.1% to about 10% of a blooming perfume composition comprising at least about 50%, more preferably at least about 60 wt. %, and even more preferably at least about 70 wt. % of blooming perfume ingredients selected from the group consisting of: ingredients having a boiling point of less than about 260° C., preferably less than about 255° C.; and more preferably less than about 250° C., and a ClogP of at least about 3, preferably more than about 3.1, and even more preferably more than about 3.2 and wherein said perfume composition comprises at least 5, preferably at least 6, more preferably at least 7, and even more preferably at least 8 or 9 or 10 or more different blooming perfume ingredients;

(2) a cleaning system comprising: detergent surfactant, perferably of the amphoteric type, and detergent builder, preferably polycarboxylate chelating agent, the ratio of said surfactant to said builder/chelating agent being from about 1:100 to about 100:1; and (3) system for providing a concentration of from about 1 ppm to about 1000 ppm of said detergent surfactant and said builder/chelating agent in the water of said toilet bowl, said water in said toilet bowl having a pH of from about 2 to about 11, preferably from about 4 to about 9.

This invention relates to improved cleaning systems for toilet bowls that include blooming perfume compositions. The blooming nature of the perfume acts to provide a positive scent signal to the consumer. The cleaning systems are especially useful in toilet bowl block detergent compositions of the "tank" or of the "rim-block" types. Such block detergent compositions contain the cleaning system comprising: detergent surfactant, preferably of the amphoteric type, preferably zwitterionic, more preferably one that contains a carboxylate group and a cationic group, and even more preferably a fatty acid amidoalkylene betaine, and polycarboxylate chelating agent, preferably, citric acid, or similar polycarboxylic acid, together with a dissolution retarding system. For a rim-block type, the composition preferably comprises a combination of water soluble cellulosic polymer, more preferably hydroxyethyl cellulose or hydroxypropyl cellulose, having a Viscosity Grade, as defined by, e.g., Cellosize® by Union Carbide, of from about 40 to about 100,000 and, polyethylene glycol containing polymer, having a molecular weight of from about 1,000 to about 20,000, any perfume present being selected to be mostly hydrophobic. For an in-tank block, higher molecular weights are required, as disclosed hereinafter.

The compositions herein have a pH, in use, of from about 2 to about 11, preferably from about 4 to about 9, more preferably from about 6 to about 8. The block compositions are preferably extremely homogeneous. Homogeneity can be achieved, e.g., by milling the ingredients together to provide a matrix that contains essentially no large particles of any one ingredient. Other processes that provide similar mechanical energy, especially by shearing, can also be used. Homogeneity is determined by the smoothness of the surface, including the surface of any cross section of the block after cutting.

The process herein involves using the cleaning system on a regular basis in toilet bowls, to maintain the cleanliness of the toilet bowl, prevent buildup of soil, and provide a positive scent signal over the useful life of the block.

All percentages and ratios used herein are by weight of the total composition unless otherwise indicated. All measurements made are at ambient temperature (about 25° C.), unless otherwise designated. The invention herein can comprise, consist of, or consist essentially of, the essential components as well as the optional ingredients and components described herein.

DETAILED DESCRIPTION OF THE INVENTION

The present invention comprises a block detergent composition for keeping a toilet bowl clean comprising:

(1) from about 0.1% to about 10%, preferably from about 1% to about 8%, and more preferably from about 1% to about 7% of a blooming perfume composition comprising at least about 50%, more preferably at least about 60 wt. %, and even more preferably at least about 70 wt. % of blooming perfume ingredients selected from the group consisting of: ingredients having a boiling point of less than about 260° C., preferably less than about 255° C.; and more preferably less than about 250° C., and a ClogP of at least about 3, preferably more than about 3.1, and even more preferably more than about 3.2 and wherein said perfume composition comprises at least 5, preferably at least 6, more preferably at least 7, and even more preferably at least 8 or even 9 or 10 or more different blooming perfume ingredients;

(2) a cleaning system comprising: detergent surfactant, perferably of the amphoteric type, and detergent builder, preferably polycarboxylate chelating agent, the ratio of said surfactant to said builder/chelating agent being from about 1:100 to about 100:1; and (3) system for providing a concentration of from about 1 ppm to about 1000 ppm of said detergent surfactant and said builder/chelating agent in the water of said toilet bowl, said water in said toilet bowl having a pH of from about 2 to about 11, preferably from about 4 to about 9.

The compositions of the present invention can also include optional ingredients to enhance specific characteristics as described hereinafter.

A. Blooming Perfume Composition

Blooming perfume ingredients, as disclosed herein, can be formulated into toilet bowl detergent compositions and provide significantly better noticeability to the consumer than nonblooming perfume compositions not containing a substantial amount of blooming perfume ingredients.

A blooming perfume ingredient is characterized by its boiling point (B.P.) and its octanol/water partition coefficient (P). The octanol/water partition coefficient of a perfume ingredient is the ratio between its equilibrium concentrations in octanol and in water. The preferred perfume ingredients of this invention have a B.P., determined at the normal, standard pressure of about 760 mm Hg, of about 260° C. or lower, preferably less than about 255° C.; and more preferably less than about 250° C., and an octanol/water partition coefficent P of about 1,000 or higher. Since the partition coefficients of the preferred perfume ingredients of this invention have high values, they are more conveniently given in the form of their logarithm to the base 10, logP. Thus the preferred perfume ingredients of this invention have logP of about 3 or higher, preferably more than about 3.1, and even more preferably more than about 3.2.

Boiling points of many perfume compounds can be found in the following sources:

Properties of Organic Compounds Database CD-ROM Ver. 5.0

CRC Press

Boca Raton, Fla.

Flavor and Fragrance—1995

Aldrich Chemical Co.

Milwaukee, Wis.

STN database/on-line

Design Institute of for Physical Property Data

American Institute of Chemical Engineers

STN database/on-line Beilstein Handbook of Organic Chemistry Beilstein Information Systems Perfume and Flavor Chemicals Steffen Arctander Vol. I, II—1969

When unreported, the 760 mm boiling points of perfume ingredients can be estimated. The following computer programs are useful for estimating these boilings points:

MPBPVP Version 1.25© 1994–96 Meylan

Syracuse Research Corporation (SRC)

Syracuse, N.Y.

ZPARC

ChemLogic, Inc.

Cambridge, Mass.

The logP of many perfume ingredients has been reported; for example, the Pomona92 database, available from Daylight Chemical Information Systems, Inc. (Daylight CIS), Irvine, Calif., contains many, along with citations to the original literature. However, the logP values are most conveniently calculated by the Pomona Med. Chem./Daylight "CLOGP" program, Version 4.42 available from Biobyte Corp., Claremont, Calif. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental logP values in the selection of perfume ingredients which are useful in the present invention.

Thus, when a perfume composition which is composed of ingredients having a B.P. of about 260° C. or lower and a ClogP, or an experimental logP, of about 3 or higher, is used in a toilet bowl detergent composition, the perfume is very effusive and very noticeable when the product is used.

Table 1 gives some non-limiting examples of blooming perfume ingredients, useful in toilet bowl detergent compositions of the present invention. The toilet bowl detergent compositions of the present invention contain from about 0.1% to about 10%, preferably from about 1% to about 8%, and more preferably from about 1% to about 7% of blooming perfume composition. The blooming perfume compositions of the present invention contain at least 5 different blooming perfume ingredients, preferably at least 6 different blooming perfume ingredients, more preferably at least 7 different blooming perfume ingredients, and even more preferably at least 8 or even 9 or 10 or more different blooming perfume ingredients. Furthermore, the blooming perfume compositions of the present invention contain at least about 50 wt. % of blooming perfume ingredients, preferably at least about 55 wt. % of blooming perfume ingredients, more preferably at least about 60 wt. % of blooming perfume ingredients, and even more preferably at least about 70 wt. % or even 80% of blooming perfume ingredients. The blooming perfume compositions herein should preferably not contain any single ingredient at a level which would provide more than about 5%, by weight of that ingredient to the total toilet bowl detergent composition, preferably not more than about 4%, by weight of the composition, and even more preferably not more than about 2.5%, by weight of the total toilet bowl detergent composition.

The perfume composition itself should preferably not contain more than 60% of any single perfume ingredient.

Most common perfume ingredients which are derived from natural sources are composed of a multitude of components. For example, orange terpenes contain about 90% to about 95% d-limonene, but also contain many other minor ingredients. When each such material is used in the formulation of blooming perfume compositions of the present invention, it is counted as one ingredient, for the purpose of defining the invention. Synthetic reproductions of such natural perfume ingredients are also comprised of a multitude of components and are counted as one ingredient for the purpose of defining the invention.

Some of the blooming perfume ingredients of the present invention can optionally be replaced by "delayed blooming" perfume ingredients. The optional delayed blooming perfume ingredients of this invention have a B.P., measured at the normal, standard pressure, of about 260° C. or lower, preferably less than about 255° C.; and more preferably less than about 250° C., and a logP or ClogP of less than about 3. Thus, when a perfume composition is composed of some preferred blooming ingredients and some delayed blooming ingredients, the perfume effect is longer lasting when the product is used. Table 2 gives some non-limiting examples of optional delayed blooming perfume ingredients, useful in toilet bowl detergent compositions of the present invention. Delayed blooming perfume ingredients are used primarily in applications where the water will evaporate, thus liberating the perfume.

When delayed blooming perfume ingredients are used in combination with the blooming perfume ingredients in the blooming perfume compositions of the present invention, the weight ratio of blooming perfume ingredients to delayed blooming perfume ingredients is typically at least about 1, preferably at least about 1.3, more preferably about 1.5, and even more preferably about 2. The blooming perfume compositions contain at least about 50 wt. % of the combined blooming perfume ingredients and delayed blooming perfume ingredients, preferably at least about 55 wt. % of the combined perfume ingredients, more preferably at least about 60 wt. % of the combined perfume ingredients, and even more preferably at least about 70 wt. % of the combined perfume ingredients. When some optional delayed blooming perfume ingredients are used in combination with the blooming perfume ingredients in the blooming perfume compositions, the blooming perfume compositions of the present invention contain at least 4 different blooming perfume ingredients and 2 different delayed blooming perfume ingredients, preferably at least 5 different blooming perfume ingredients and 3 different delayed blooming perfume ingredients, and more preferably at least 6 or 7 or even 9 or 10 or more different blooming perfume ingredients and 4, preferably 5, more preferably at least 6 or 7 or even 9 or 10 or more different delayed blooming perfume ingredients.

In the perfume art, some auxiliary materials having no odor, or a low odor, are used, e.g., as solvents, diluents, extenders or fixatives. Non-limiting examples of these materials are ethyl alcohol, carbitol, dipropylene glycol, diethyl phthalate, triethyl citrate, isopropyl myristate, and benzyl benzoate. These materials are used for, e.g., solubilizing or diluting some solid or viscous perfume ingredients to, e.g., improve handling and/or formulating. These materials are useful in the blooming perfume compositions, but are not counted in the calculation of the limits for the definition/ formulation of the blooming perfume compositions of the present invention.

Non-blooming perfume ingredients, which should be minimized in toilet bowl detergent compositions of the present invention, are those having a B.P. of more than about 260° C. Table 3 gives some non-limiting examples of non-blooming perfume ingredients. In some particular toilet bowl detergent compositions, some non-blooming perfume ingredients can be used in small amounts, e.g., to improve product odor.

In the following tables, measured boiling points are taken from the following sources:

Properties of Organic Compounds Database CD-ROM Ver. 5.0

CRC Press

Boca Raton, Fla.

Flavor and Fragrance—1995

Aldrich Chemical Co.

Milwaukee, Wis.

STN database/on-line

Design Institute of for Physical Property Data

American Institute of Chemical Engineers

STN database/on-line

Beilstein Handbook or Organic Chemistry

Beilstein Information Systems

Perfume and Flavor Chemicals

Steffen Arctander

Vol. I, II—1969

Estimated boilings points are an average of those determined by the following computer programs:

MPBPVP Version 1.25© 1994–96 Meylan

Syracuse Research Corporation (SRC)

ZPARC

ChemLogic, Inc.

The predicted ClogP at 25° C. was determined by the following computer program:

Panoma MedChem/Daylight ClogP V. 4.42

TABLE 1

Sample of Blooming Perfume Ingredients

| Ingredient | ClogP (Pred.) | Boiling Pt. (Meas.) | Boiling Pt. (Pred.) |
|---|---|---|---|
| Alio-ocimene | 4.36 | | 195 |
| Allyl cyclohexanepropionate | 3.94 | | 252 |
| Allyl heptanoate | 3.40 | | 209 |
| trans-Anethole | 3.31 | 232 | |
| Benzyl butyrate | 3.02 | 240 | |
| Camphene | 4.18 | 160 | |
| Cadinene | 7.27 | | 252 |
| Carvacrol | 3.40 | 238 | |
| cis-3-Hexenyl tiglate | 3.80 | | 225 |
| Citronellol | 3.25 | 223 | |
| Citronellyl acetate | 4.20 | 234 | |
| Citronellyl nitrile | 3.09 | 226 | |
| Citronellyl propionate | 4.73 | | 257 |
| Cyclohexylethyl acetate | 3.36 | 222 | |
| Decyl Aldehyde (Capraldehyde) | 4.01 | 208 | |
| Dihydromyrcenol | 3.03 | 192 | |
| Dihydromyrcenyl acetate | 3.98 | | 221 |
| 3,7-Dimethyl-1-octanol | 3.74 | 205 | |
| Diphenyloxide | 4.24 | 259 | |
| Fenchyl Acetate (1,3,3-Trimethyl-2-norbornanyl acetate) | 3.53 | | 234 |
| Geranyl acetate | 3.72 | 233 | |
| Geranyl formate | 3.27 | | 231 |
| Geranyl nitrile | 3.25 | 228 | |
| cis-3-Hexenyl isobutyrate | 3.27 | | 204 |
| Hexyl Neopentanoate | 4.06 | | 213 |
| Hexyl tiglate | 4.28 | | 221 |
| alpha-Ionone | 3.70 | 237 | |
| Isobornyl acetate | 3.53 | 238 | |

TABLE 1-continued

Sample of Blooming Perfume Ingredients

| Ingredient | ClogP (Pred.) | Boiling Pt. (Meas.) | Boiling Pt. (Pred.) |
|---|---|---|---|
| Isobutyl benzoate | 3.57 | 242 | |
| Isononyl acetate | 4.28 | | 220 |
| Isononyl alcohol (3,5,5-Trimethyl-1-hexanol) | 3.08 | 194 | |
| Isopulegyl acetate | 3.70 | | 243 |
| Lauraldehyde | 5.07 | 250 | |
| d-Limonene | 4.35 | 177 | |
| Linalyl acetate | 3.50 | | 230 |
| (−)-L-Menthyl acetate | 4.18 | 227 | |
| Methyl Chavicol (Estragole) | 3.13 | 216 | |
| Methyl n-nonyl acetaldehyde | 4.85 | 247 | |
| Methyl octyl acetaldehyde | 4.32 | | 224 |
| beta--Myrcene | 4.33 | | 165 |
| Neryl acetate | 3.72 | 236 | |
| Nonyl acetate | 4.41 | 229 | |
| Nonaldehyde | 3.48 | 191 | |
| p-Cymene | 4.07 | 173 | |
| alpha-Pinene | 4.18 | 156 | |
| beta--Pinene | 4.18 | 166 | |
| alpha-Terpinene | 4.41 | 175 | |
| gamma-Terpinene | 4.35 | 183 | |
| alpha-Terpinyl acetate | 3.58 | 220 | |
| Tetrahydrolinalool | 3.52 | 202 | |
| Tetrahydromyrcenol | 3.52 | 195 | |
| 2-Undecenal | 4.22 | | 235 |
| Verdox (o-t-Butylcyclohexyl acetate) | 4.06 | | 239 |
| Vertenex (4-tert.Butylcyclohexyl acetate) | 4.06 | | 237 |

TABLE 2

Examples of "Delayed Blooming" Perfume Ingredients

| Ingredient | ClogP (Pred.) | Boiling Pt. (Meas.) | Boiling Pt. (Pred.) |
|---|---|---|---|
| Allyl caproate | 2.87 | 186 | |
| Amyl acetate (n-Pentyl acetate) | 2.30 | 147 | |
| Amyl Propionate | 2.83 | 169 | |
| p-Anisaldehyde | 1.78 | 249 | |
| Anisole | 2.06 | 154 | |
| Benzaldehyde (Benzenecarboxaldehyde) | 1.50 | 179 | |
| Benzyl acetate | 1.96 | 211 | |
| Benzylacetone | 1.74 | 234 | |
| Benzyl alcohol | 1.10 | 205 | |
| Benzyl formate | 1.50 | 203 | |
| Benzyl isovalerate | 3.42 | | 256 |
| Benzyl propionate | 2.49 | 221 | |
| beta-gamma-Hexenol (2-Hexen-1-ol) | 1.40 | | 164 |
| (+)-Camphor | 2.18 | 207 | |
| (+)-Carvone | 2.01 | 231 | |
| L-Carvone | 2.01 | | 230 |
| Cinnamic alcohol | 1.41 | | 258 |
| Cinnamyl formate | 1.91 | 252 | |
| cis-Jasmone | 2.64 | | 253 |
| cis-3-Hexenyl acetate | 2.34 | | 175 |
| Citral (Neral) | 2.95 | 208 | |
| Cumic alcohol | 2.53 | 249 | |
| Cuminaldehyde | 2.92 | 235 | |
| Cyclal(2,4-Dimethyl-3-cyclohexene-1-carboxaldehyde) | 2.36 | | 203 |
| Dimethyl benzyl carbinol | 1.89 | 215 | |
| Dimethyl benzyl carbinyl acetate | 2.84 | | 248 |
| Ethyl acetate | 0.71 | 77 | |
| Ethyl acetoacetate | 0.33 | 181 | |
| Ethyl amyl ketone | 2.44 | 167 | |
| Ethyl benzoate | 2.64 | 215 | |
| Ethyl butanoate | 1.77 | 121 | |
| 3-Nonanone (Ethyl hexyl ketone) | 2.97 | 187 | |
| Ethyl phenylacetate | 2.35 | 228 | |
| Eucalyptol | 2.76 | 176 | |

TABLE 2-continued

Examples of "Delayed Blooming" Perfume Ingredients

| Ingredient | ClogP (Pred.) | Boiling Pt. (Meas.) | Boiling Pt. (Pred.) |
|---|---|---|---|
| Eugenol | 2.40 | 253 | |
| Fenchyl alcohol | 2.58 | 199 | |
| Flor Acetate (Tricyclodecenyl acetate) | 2.36 | | 233 |
| Frutene (Tricyclodecenyl propionate) | 2.89 | | 250 |
| gamma-Nonalactone | 2.77 | 243 | |
| trans-Geraniol | 2.77 | 230 | |
| cis-3-Hexen-1-ol/Leaf Alcohol | 1.40 | 156 | |
| Hexyl acetate | 2.83 | 171 | |
| Hexyl formate | 2.38 | 155 | |
| Hydratopic alcohol | 1.58 | | 233 |
| Hydroxycitronellal | 1.54 | 241 | |
| Indole (2,3-Benzopyrrole) | 2.13 | 254 | |
| Isoamyl alcohol | 1.22 | 131 | |
| Isopropyl phenylacetate | 2.66 | | 237 |
| Isopulegol | 2.75 | | 231 |
| Isoquinoline (Benzopyridine) | 1.82 | 243 | |
| Ligustrai (2,4-Dimethyl-3-Cyclohexene-1-carboxaldehyde) | 2.36 | | 204 |
| Linalool | 2.55 | 193 | |
| Linalool oxide | 1.45 | | 223 |
| Linalyl formate | 3.05 | | 212 |
| Menthone | 2.83 | | 214 |
| 4-Methylacetophenone | 2.08 | 226 | |
| Methyl pentyl ketone | 1.91 | 151 | |
| Methyl anthranilate | 2.02 | 256 | |
| Methyl benzoate | 2.11 | 199 | |
| Methyl Phenyl Carbinyl Acetate (alpha-Methylbenzyl acetate) | 2.27 | | 216 |
| Methyl Eugenol (Eugenyl methyl ether) | 2.67 | 254 | |
| Methyl Heptenone (6-Methyl-5-hepten-2-one) | 1.82 | 173 | |
| Methyl Heptine Carbonate (Methyl 2-octynoate) | 2.57 | 218 | |
| Methyl Heptyl ketone | 2.97 | 195 | |
| Methyl Hexyl ketone | 2.44 | 173 | |
| Methyl salicylate | 2.45 | 223 | |
| Dimethyl anthranilate | 2.16 | 255 | |
| Nerol | 2.77 | 225 | |
| delta-Nonalactone | 2.80 | | 226 |
| gamma-Octalactone | 2.24 | 256 | |
| 2-Octanol | 2.72 | 180 | |
| Octyl Aldehyde (Caprylic aldehyde) | 2.95 | 167 | |
| p-Cresol | 1.97 | 202 | |
| p-Cresyl methyl ether | 2.56 | 175 | |
| Acetanisole | 1.80 | 258 | |
| 2-Phenoxyethanol | 1.19 | 245 | |
| Phenylacetaldehyde | 1.78 | 195 | |
| 2-Phenylethyl acetate | 2.13 | 235 | |
| Phenethyl alcohol | 1.18 | 218 | |
| Phenyl Ethyl dimethyl Carbinol (Benzyl-tert-butanol) | 2.42 | | 257 |
| Prenyl acetate | 1.68 | | 150 |
| Propylbutanoate | 2.30 | 143 | |
| (+)-Pulegone | 2.50 | 224 | |
| Rose oxide | 2.90 | | 197 |
| Safrole | 2.57 | 235 | |
| 4-Terpinenol | 2.75 | 211 | |
| Terpinolene (alpha-Terpineol) | 2.63 | 219 | |
| Veratrole (1,2-Dimethoxybenzene) | 1.60 | 206 | |
| Viridine (Phenylacetaldehyde dimethyl acetal) | 1.29 | 220 | |

TABLE 3

Examples of "Non Blooming" Perfume Ingredients

| Ingredient | ClogP (Pred.) | Boiling Pt. (Meas.) | Boiling Pt. (Pred.) |
|---|---|---|---|
| (Ambrettolide) Oxacycloheptadec-10-en-2-one | 6.36 | | 352 |
| (Amyl benzoate) n-Pentyl benzoate | 4.23 | | 263 |
| Isoamyl cinnamate | 4.45 | | 300 |
| alpha-Amylcinnamaldehyde | 4.32 | 289 | |
| alpha-Amylcinnamaldehyde dimethyl acetal | 4.03 | | 320 |
| (iso-Amyl Salicylate) isopentyl salicylate | 4.43 | 277 | |
| (Aurantiol) Methyl anthranilate/hydroxycitronellal Schiff base | 4.22 | | 413 |
| Benzophenone | 3.18 | 305 | |
| Benzyl salicylate | 4.21 | 320 | |
| beta-Caryophyllene | 6.45 | | 263 |
| Cedrol | 4.53 | | 274 |
| Cedryl acetate | 5.48 | | 289 |
| Cinnamyl cinnamate | 4.64 | | 387 |
| Citronellyl isobutyrate | 5.04 | | 266 |
| Coumarin | 1.41 | 302 | |
| Cyclohexyl salicylate | 4.48 | | 327 |
| Cyclamen aldehyde | 3.46 | | 271 |
| delta-Dodecalactone | 4.39 | | 279 |
| (Dihydro Isojasmonate) Methyl 2-hexyl-3-oxo-cyclopentanecarboxylate | 3.09 | | 314 |
| Diphenylmethane | 4.06 | 265 | |
| Ethylene brassylate | 4.62 | | 390 |
| Ethyl methylphenylglycidate | 2.71 | 274 | |
| Ethyl undecylenate | 4.99 | 261 | |
| Ethyl Vanillin | 1.80 | 285 | |
| Isoeugenol | 2.58 | 266 | |
| Iso E Super | 4.85 | | 307 |
| (Exaltolide) Pentadecanolide | 6.29 | | 338 |
| (Galaxolide) 4,6,6,7,8,8-Hexamethyl-1,3,4,6,7,8-hexahydro-cyclopenta(G)-2-benzopyran | 6.06 | | 335 |
| gamma-Methyl Ionone (alpha-Isomethylionone) | 4.02 | | 278 |
| Geranyl isobutyrate | 5.00 | | 295 |
| Hexadecanolide | 6.85 | | 352 |
| cis-3-Hexenyl salicylate | 4.61 | | 323 |
| alpha-Hexylcinnamaldehyde | 4.85 | | 334 |
| n-Hexyl salicylate | 5.09 | | 318 |
| alpha---Irone | 4.23 | | 279 |
| 6-Isobutylquinoline | 3.99 | | 294 |
| Lilial (p-tert.Butyl-alpha-methyldihydrocinnamic aldehyde, PT Bucinol) | 3.86 | | 282 |
| Linalyl benzoate | 5.42 | | 325 |
| (2-Methoxy Naphthalene) beta-Naphthyl methyl ether | 3.24 | 274 | |
| Methyl cinnamate | 2.47 | 262 | |
| Methyl dihydrojasmonate | 2.42 | | 314 |
| Methyl beta-naphthyl ketone | 2.76 | 302 | |
| 10-Oxahexadecanolide | 4.38 | | 355 |
| Patchouli alcohol | 4.53 | | 317 |
| (Phantolide) 5-Acetyl-1,1,2,3,3,6-hexamethylindan | 5.69 | | 333 |
| Phenethyl benzoate | 4.06 | | 335 |
| Phenethyl phenylacetate | 3.77 | | 350 |
| Phenyl Hexanol (3-Methyl-5-phenyl-1-pentanol) | 3.17 | | 296 |
| Tonalid (7-Acetyl-1,1,3,4,4,6-hexamethyltetralin) | 6.25 | | 344 |
| delta-Undecalactone | 3.86 | | 262 |
| gamma-Undecalactone | 3.83 | 286 | |
| Vanillin | 1.28 | 285 | |
| Vertinert Acetate | 5.47 | | 332 |

The perfumes suitable for use in the toilet bowl detergent composition can be formulated from known fragrance ingredients and for purposes of enhancing environmental compatibility, the perfume is preferably substantially free of halogenated fragrance materials and nitromusks.

1. Optional protective perfume carrier

The compositions and articles of this invention contain an effective amount of various moisture-activated encapsulated perfume particles, as an optional ingredient. The encapsulated particles act as protective carriers and reduce the loss of perfume prior to use. Such materials include, for example, cyclodextrin/perfume inclusion complexes, polysaccharide cellular matrix perfume microcapsules, and the like. Encapsulation of perfume minimizes the diffusion and loss of the volatile blooming perfume ingredients. Perfume is released when the materials are wetted, to provide a pleasant odor signal in use. Especially preferred are cyclodextrin inclusion complexes.

The optional water-activated protective perfume carriers are very useful in the present invention. They allow the use of lower level of perfume in the detergent blocks because of the reduced loss of the perfume during manufacturing and use. Furthermore, since the protected perfume is used in the form of a dry powder, instead of a liquid, the toilet bowl detergent compositions have a more rigid structure. The more rigid structure lasts longer during use, especially if the detergent compositions are made by a tableting process.

Due to the minimal loss of the volatile ingredients of the blooming perfume compositions provided by the water activated protective perfume carrier, the perfume compositions that incorporate them can contain less blooming perfume ingredients than those used in the free, unencapsulated form. The encapsulated and/or complexed perfume compositions typically contain at least about 20%, preferably at least about 30%, and more preferably at least about 40% blooming perfume ingredients. Optionally, but preferably, compositions that contain encapsulated and/or complexed perfume also comprise free perfume in order to provide consumers with a positive scent signal before the composition is used.

a. Cyclodextrin

As used herein, the term "cyclodextrin" includes any of the known cyclodextrins such as unsubstituted cyclodextrins containing from six to twelve glucose units, especially, alpha-, beta-, and gamma-cyclodextrins, and/or their derivatives, and/or mixtures thereof. The alpha-cyclodextrin consists of 6, the beta-cyclodextrin 7, and the gamma-cyclodextrin 8, glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. These cavities can be filled with all or a portion of an organic molecule with suitable size to form an "inclusion complex." Alpha-, beta-, and gamma-cyclodextrins can be obtained from, among others, American Maize-Products Company (Amaizo), Hammond, Ind.

Cyclodextrin derivatives are disclosed in U.S. Pat. No. 3,426,011, Parmerter et al., issued Feb. 4, 1969; U.S. Pat. Nos. 3,453,257, 3,453,258, 3,453,259, and 3,453,260, all in the names of Parmerter et al., and all also issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,638,058, Brandt et al., issued Jan. 20, 1987; U.S. Pat. No. 4,746,734, Tsuchiyama et al., issued May 24, 1988; and U.S. Pat. No. 4,678,598, Ogino et al., issued Jul. 7, 1987, all of said patents being incorporated herein by reference. Examples of cyclodextrin derivatives suitable for use herein are methyl-beta-cyclodextrin, hydroxyethyl-beta-cyclodextrin, and hydroxypropyl-beta-cyclodextrin of different degrees of substitution (D.S.), available from Amaizo; Wacker Chemicals (USA), Inc.; and Aldrich Chemical Company. Water-soluble derivatives are also highly desirable.

The individual cyclodextrins can also be linked together, e.g., using multifunctional agents to form oligomers, polymers, etc. Examples of such materials are available commercially from Amaizo and from Aldrich Chemical Company (beta-cyclodextrin/epichlorohydrin copolymers).

The preferred cyclodextrin is beta-cyclodextrin. It is also desirable to use mixtures of cyclodextrins. Preferably at least a major portion of the cyclodextrins are alpha-, beta- and/or gamma-cyclodextrins, more preferably alpha- and beta-cyclodextrins. Some cyclodextrin mixtures are commercially available from, e.g., Ensuiko Sugar Refining Company, Yokohama, Japan.

b. Formation of Cyclodextrin/Perfume Inclusion Complexes

The perfume/cyclodextrin inclusion complexes of this invention are formed in any of the ways known in the art. Typically, the complexes are formed either by bringing the perfume and the cyclodextrin together in a suitable solvent, e.g., water, or, preferably, by kneading/slurrying the ingredients together in the presence of a suitable, preferably minimal, amount of solvent, preferably water. The kneading/slurrying method is particularly desirable because it produces smaller complex particles and requires the use of less solvent, eliminating or reducing the need to further reduce particle size and separate excess solvent. Disclosures of complex formation can be found in Atwood, J. L., J. E. D. Davies & D. D. MacNichol, (Ed.): *Inclusion Compounds Vol. III*, Academic Press (1984), especially Chapter 11, Atwood, J. L. and J. E. D. Davies (Ed.): *Proceedings of the Second International Symposium of Cyclodextrins* Tokyo, Japan, (July, 1984), and J. Szejtli, *Cyclodextrin Technology*, Kluwer Academic Publishers (1988), said publications incorporated herein by reference.

In general, perfume/cyclodextrin complexes have a molar ratio of perfume compound to cyclodextrin of about 1:1. However, the molar ratio can be either higher or lower, depending on the size of the perfume compound and the identity of the cyclodextrin compound. The molar ratio can be determined by forming a saturated solution of the cyclodextrin and adding the perfume to form the complex. In general the complex will precipitate readily. If not, the complex can usually be precipitated by the addition of electrolyte, change of pH, cooling, etc. The complex can then be analyzed to determine the ratio of perfume to cyclodextrin.

As stated hereinbefore, the actual complexes are determined by the size of the cavity in the cyclodextrin and the size of the perfume molecule. Desirable complexes can be formed using mixtures of cyclodextrins since perfumes are normally mixtures of materials that vary widely in size. It is usually desirable that at least a majority of the material be alpha-, beta-, and/or gamma-cyclodextrin, more preferably beta-cyclodextrin. The content of the perfume in the beta-cyclodextrin complex is typically from about 5% to about 15%, more normally from about 7% to about 12%.

Continuous complexation operation usually involves the use of supersaturated solutions, kneading/slurrying method, and/or temperature manipulation, e.g., heating and then either cooling, freeze-drying, etc. The complexes are dried to a dry powder to make the desired composition. In general, the fewest possible process steps are preferred to avoid loss of perfume.

c. Matrix Perfume Microcapsules

Water-soluble cellular matrix perfume microcapsules are solid particles containing perfume stably held in the cells. The water-soluble matrix material comprises mainly polysaccharide and polyhydroxy compounds. The polysaccharides are preferably higher polysaccharides of the non-sweet, colloidally-soluble types, such as natural gums, e.g., gum arabic, starch derivatives, dextrinized and hydrolyzed starches, and the like. The polyhydroxy compounds are preferably alcohols, plant-type sugars, lactones, monoethers, and acetals. The cellular matrix microcapsules useful in the present invention are prepared by, e.g., (1) forming an aqueous phase of the polysaccharide and polyhydroxy compound in proper proportions, with added emulsifier if necessary or desirable; (2) emulsifying the perfumes in the aqueous phase; and (3) removing moisture while the mass is plastic or flowable, e.g., by spray drying droplets of the emulsion. The matrix materials and process details are disclosed in, e.g., U.S. Pat. No. 3,971,852, Brenner et al., issued Jul. 27, 1976, which is incorporated herein by reference.

The present invention preferably has minimal non-encapsulated surface perfume, preferably less than about 1%.

Moisture-activated perfume microcapsules can be obtained commercially, e.g., as IN-CAP® from Polak's Frutal Works, Inc., Middletown, N.Y.; and as Optilok System® encapsulated perfumes from Encapsulated Technology, Inc., Nyack, N.Y.

Water-soluble matrix perfume microcapsules preferably have size of from about 0.5 micron to about 300 microns, more preferably from about 1 micron to about 200 microns, most preferably from about 2 microns to about 100 microns.

B. The Cleaning System

Detergents surfactants comprise the anionic, nonionic, cationic and amphoteric detergent surfactants. Suitable surfactants are described in the patents incorporated herein by reference, especially U.S. Pat. No. 4,480,490, and U.S. Pat. No. 4,722,802. However, amphoteric surfactantsare preferred.

Amphoteric, e.g., Zwitterionic Detergent Surfactants

Zwitterionic detergent surfactants contain both cationic and anionic hydrophilic groups on the same molecule at a relatively wide range of pH's. The typical cationic group is a quaternary ammonium group, although other positively charged groups like sulfonium and phosphonium groups can also be used. The typical anionic hydrophilic groups are carboxylates and sulfonates, although other groups like sulfates, phosphates, etc., can be used. A generic formula for some preferred zwitterionic detergent surfactants is:

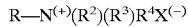

wherein R is a hydrophobic group; $R^2$ and $R^3$ are each $C_{1-4}$ alkyl, hydroxy alkyl or other substituted alkyl group which can also be joined to form ring structures with the N; $R^4$ is a moiety joining the cationic nitrogen atom to the hydrophilic group and is typically an alkylene, hydroxy alkylene, or polyalkoxy group wherein the group contains from about one to about four carbon atoms; and X is the hydrophilic group which is preferably a carboxylate or sulfonate group.

Preferred hydrophobic groups R are alkyl groups containing from about 8 to about 22, preferably less than about 18, more preferably less than about 16, carbon atoms. The hydrophobic group can contain unsaturation and/or substituents and/or linking groups such as aryl groups, amido groups, ester groups, etc. In general, fatty acyl amido alkylene groups are preferred.

A specific "simple" zwitterionic detergent surfactant is 3-(N-dodecyl-N,N-dimethyl)-2-hydroxy-propane-1-sulfonate, available from the Sherex Company under the trade name "Varion HC."

Other specific zwitterionic detergent surfactants have the generic formula:

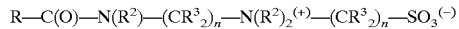

wherein each R is a hydrocarbon, e.g., an alkyl group containing from about 8 up to about 20, preferably up to about 18, more preferably up to about 16 carbon atoms, each $(R^2)$ is either a hydrogen (when attached to the amido nitrogen), short chain alkyl or substituted alkyl containing from one to about four carbon atoms, preferably groups selected from the group consisting of methyl, ethyl, propyl, hydroxy substituted ethyl or propyl and mixtures thereof, preferably methyl, each $(R^3)$ is selected from the group consisting of hydrogen and hydroxy groups, and each n is a number from 1 to about 4, preferably from 2 to about 3; more preferably about 3, with no more than about one hydroxy group in any $(CR^3_2)$ moiety. The R groups can be branched and/or unsaturated, and such structures can provide spotting/filming benefits, even when used as part of a mixture with straight chain alkyl R groups. The $R^2$ groups can also be connected to form ring structures. A detergent surfactant of this type is a $C_{10-14}$ fatty acylamidopropylene (hydroxypropylene)sulfobetaine that is available from the Sherex Company under the trade name "Varion CAS Sulfobetaine".

Other zwitterionic detergent surfactants useful, and, surprisingly, preferred, herein include hydrocarbyl, e.g., fattyacylamidoalkylene betaines. These detergent surfactants, which are more cationic at the pH of the composition, have the generic formula:

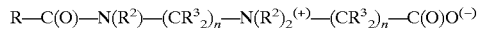

wherein each R is a hydrocarbon, e.g., an alkyl group containing from about 8 up to about 20, preferably up to about 18, more preferably up to about 16 carbon atoms, each $(R^2)$ is either a hydrogen (when attached to the amido nitrogen), short chain alkyl, or substituted alkyl, containing from one to about four carbon atoms, preferably groups selected from the group consisting of methyl, ethyl, propyl, hydroxy substituted ethyl or propyl and mixtures thereof, preferably methyl, each $(R^3)$ is selected from the group consisting of hydrogen and hydroxy groups, and each n is a number from 1 to about 4, preferably from 2 to about 3; more preferably about 3, with no more than about one hydroxy group in any $(CR^3_2)$ moiety. The R groups can be branched and/or unsaturated, and such structures can provide spotting/filming benefits, even when used as part of a mixture with straight chain alkyl R groups.

An example of such a detergent surfactant is a $C_{12-16}$ fatty acylamidopropylbetaine available in a preferred powder form from Goldschmidt under the trade name "Tego Betaine D."

The level of surfactant is from about 10% to about 90% by weight, preferably from about 15 to about 50% by weight, and most preferably from about 20% to about 35% by weight. At the pH of the composition in use, the carboxyl group is substantially nonionic, although some portion is ionized to create a negative charge.

The cleaning system also comprises polycarboxylic acid having strong chelating properties for calcium at the use pH, e.g., citric acid, or salt thereof, preferably sodium or potassium, or an equivalent polycarboxylic acid, or salt thereof. Equivalent polycarboxylic acids have similar calcium binding constants and include, for example, succinic, glutaric, adipic, maleic, etc. The level of polycarboxylic, e.g., citric acid, is preferably from about 10% to about 90% by weight, preferably from about 15% to about 50% by weight, and most preferably from about 20% to about 40% by weight.

The combination of amphoteric/betaine detergent surfactant and polcarboxylic/citric acid type of chelating agent provides an unusually effective cleaning effect that prolongs the time that the bowl remains clean without need for mechanical cleaning effort.

The cleaning system preferably does not include any of the solid bleaching agents, especially chlorine bleaching agents, or phosphorous containing cleaning ingredients. The materials in the composition are preferably biodegradable to the maximum extent possible and are preferably safe to use. It is desirable that such compositions not pose a threat to pets.

The Dissolution Retarding System

The dissolution retarding system for block detergent compositions can be any one of the systems disclosed in the art incorporated by reference herein, or hereafter. Preferably the dissolution system comprises water soluble cellulosic material. The primary dissolution retarding agent is preferably either hydroxypropyl cellulose or hydroxyethyl cellulose. The secondary dissolution retarding agent is preferably polyethylene glycol, or a polymer that contains a major percentage of polyethylene glycol, so that the polymer has the characteristics of polyethylene glycol. Mixtures of these agents are preferably present in the block at a level of from about 5% to about 60% by weight, and, especially for "in tank" blocks, preferably from about 10% to about 50% by weight, and most preferably from about 20% to about 40% by weight. In tank blocks require more dissolution retarding agent since they are in water for the longest time. Both of these agents are non-ionic, water soluble, acid stable polymers and have the capacity of acting as dissolution retarding agents.

For rim-block types, preferably the hydroxyethyl and/or hydroxypropyl cellulose has a Viscosity Grade, as defined in the Union Carbide publication Cellosize, of from about 40 to about 100,000, preferably from about 10,000 to about 30,000, and has a degree of hydroxyethyl or hydroxypropyl substitution of from about 0.5 to about 2.5, preferably from about 0.85 to about 1.55, and more preferably from about 0.9 to about 1. The polyethylene glycol has a molecular weight from about 1,000 to about 20,000, preferably form about 2,000 to about 8,000.

For in-tank block types, preferably higher molecular weights are preferred. Typically, the cellulosic polymers are those that have a Brookfield viscosity at 25° C. and at 1% concentration in water of from about 1,000 to about 5,000, e.g., Natrosol® brand grades of from MH to HH, available from Hercules, Inc. Similarly, the other polymer is poly (ethylene oxide) which has a molecular weight of from about $2 \times 10^5$ to about $5 \times 10^6$ preferably from about $1 \times 10^6$ to about $5 \times 10^6$, e.g., Polyox® WSR-301 or Polyox Coagulant from Union Carbide.

The ratio of cellulosic material to polyethylene glycol (or their equivalents) is from about 0.1 to about $\infty$, preferably from about 0.5 to about 30, more preferably from about 1 to about 10.

Other dissolution retarding agents can be present. Other dissolution retarding agent modifiers include water dispersible, acid stable polyalkoxylated cetyl alcohol or stearyl alcohol, or a mixture thereof, containing from about 2 to about 8 alkyleneoxy units per molecule, preferably from about 4 to about 6 units, and having a molecular weight of from about 360 to about 650. The alkyleneoxy units are preferably ethyleneoxy. The level of dissolution is controlled to provide a level of cleaning actives (cleaning system ingredients) in the toilet bowl water of from about 1 ppm to about 1000 ppm, preferably from about 5 ppm to about 50 ppm, more preferably from about 10 ppm to about 30 ppm, the ratio of detergent surfactant to polycarboxylic acid being from about 1:100 to about 100:1, preferably from about 1:10 to about 10:1, and more preferably from about 1:3 to about 3:1.

The rate of dissolution for block detergent compositions can be adjusted by incorporating larger or smaller amounts of the various dissolution retarding agents to provide lesser and greater rates of dissolution. For example, for any given hanger that holds the block, and for any given type of toilet which has a given flow of water, there will be an optimum dissolution rate. In general, the cellulosic material will provide the greatest resistance to dissolution. The polyethylene glycol will provide less resistance, and the perfume selection and homogeneity will affect the dissolution rate. Within the limits given herein before, one can adjust the dissolution system based upon the level of cleaning system actives, the surface area of the block that is exposed to the water flow by the hanger, the type and level of perfume present, and the desired level of cleaning ingredients in the bowl water. By adjusting the amounts and identities of erosion rate modifiers, the dissolution rate can be readily adjusted to create the desired level of cleaning ingredients in the bowl. The life of the block can be varied from about one to about five months by adjusting the size of the block.

Optional Ingredients

The detergent compositions of the present invention may optionally contain a chlorine bleach material which provides from about 0.003% to about 4% available chlorine based on the weight of the composition, preferably from about 0.01% to about 2%, more preferably from about 0.05% to about 1%, more preferably still from about 0.1% to about 0.5%.

Methods for determining "available chlorine" of compositions incorporating chlorine bleach materials are well known in the art. Available chlorine is the chlorine which can be liberated by acidification of an aqueous solution of hypochlorite ions (or a material that can form hypochlorite ions in aqueous solution) and at least a molar equivalent amount of chloride ions. Numerous materials are known which provide available chlorine.

A conventional analytical method for determining available chlorine is by addition of an excess of an iodide salt and titration of the liberated free iodine with a reducing agent, such as sodium thiosulfate. Samples of the detergent compositions are typically dissolved in a water-chloroform mixture to extract any interfering organics, prior to analyzing for available chlorine. An aqueous solution containing about 1% of the subject composition is used to determine available chlorine of the composition.

Many chlorine bleach materials are known, such as disclosed in Mizuno, W. G., "Dishwashing", *Detergency: Theory and Test Methods*, Surfactant Science Series, Volume 5, Part III, pages 872–878. Chlorine bleach materials useful in the subject invention compositions include alkali metal hypochlorites, hypochlorite addition products, and N-chloro compounds usually containing an organic radical. N-chloro compounds are usually characterized by a double bond on the atom adjacent to a trivalent nitrogen and a chlorine ($Cl^+$) attached to the nitrogen which is readily exchanges with $H^+$ or $M^+$ (where $M^+$ is a common metal ion such as $Na^+$, $K^+$, etc.), so as to release HOCl or $OCl^-$ on hydrolysis.

Preferred alkali metal hypochorite compounds useful in the detergent compositions herein include sodium hypochlorite, potassium hypochlorite, and lithium hypochlorite. Although known as chlorine bleach materials, alkaline earth metal hypochlorites, such as calcium hypochlorite and magnesium hypochlorite, are not preferred for the present compositions due to poor compatibility of the alkaline earth metal cations with the anionic surfactants.

A preferred hypochlorite addition product useful in the detergent compositions of this invention is chlorinated trisodium phosphate which is a crystalline hydrated double salt of trisodium phosphate and sodium hypochlorite, which is prepared by crystallizing from an aqueous blend of sodium hypochlorite, castic soda, trisodium phosphate, and disodium phosphate. Chlorinated trisodium phosphate is typically commercially available as chlorinated trisodium phosphate dodecahydrate.

Examples of N-chloro compounds useful as chlorine bleach materials in the subject compositions include trichlorolisocyanuric acid, dichloroisocynauric acid, monochloroisocyanuric acid, 1,3-dichloro-5,5-dimethylhydantoin, 1-chloro-5,5-dimethylhydantoin, N-chlorosuccinimide, N-chlorosulfamate, N-chloro-p-nitroacetanilide, N-chloro-o-nitroacetanilide, N-chloro-m-nitroacetanilide, N-m-dichloroacetanilide, N-p-dichloroacetanilide, Dichloramine-T, N-chloro-propionanilide, N-chlorobutyranilide, N-chloroacetanilide, N-o-dichloroacetanilide, N-chloro-p-acetotoluide, N-chloro-m-acetotoluide, N-chloroformanilide, N-chloro-o-acetotoluide, Chloramine-T, ammonia monochloramine, albuminoid chloramines, N-chlorosulfamide, Chloramine B, Dichloramine B, Di-Halo (bromochlorodimethylhydantoin), N,N'-dichlorobenzoylene urea, p-toluene sulfodichloroamide, trichloromelamine, N-chloroammeline, N,N'-dichloroazodicarbonamide, N-chloroacetyl urea, N,N'-dichlorobiuret, chlorinated dicyandiamide, and alkali metal salts of the above acids, and stable hydrates of the above compounds.

Particularly preferred chlorine bleach materials useful in the detergent compositions herein are chloroisocynanuric acids and alkali metal salts thereof, preferably potassium, and especially sodium salts thereof. Examples of such compounds include trichloroisocyananuric acid, dichloroisocyanuric acid, sodium dichloroisocyanurate, potassium dichloroisocyanurate, and trichloro-potassium dichloroisocynanurate complex. The most preferred chlorine bleach material is sodium dichloroisocyanurate; the dihydrate of this material is particularly preferred due to its excellent stability.

The composition according to the invention can also, preferably, comprise one or more additional ingredients such as, for example, bactericides, bacteriostats, hard water film inhibitors, stain inhibitors and dyes. These additional ingredients can be present in the composition in total amounts of from about 0.1% to about 20% by weight, preferably about 1% to about 15% by weight and most preferably about 3% to about 10% by weight of the composition.

Bactericides and bacteriostats are those agents which inhibit and kill germs and other undesirable organisms. These may include, for example, quaternary ammonium materials, oxygen bleaches like monopersulfates (typically potassium salts), etc. as well as others known to those skilled in the art. In general, however, these are not needed in the present invention.

Hard water inhibitors and stain inhibitors may include polymers such as sodium polyacrylates or copolymers of maleic and acrylic acids.

Dyes are those ingredients which typically impart a pleasing color to the composition, and can include any of the known blue, green or violet dyes.

Process for Manufacture

Although the solid block, controlled release compositions herein can be prepared by any known process, such as casting, molding or tablet compression, the compositions are preferably prepared by imparting mechanical energy and shearing forces to the composition, e.g., by milling the various ingredients, to effect a highly homogeneous mass and then extruding the mass. The extruded shape is then cut into convenient sizes, stamped, if desired, and packaged, preferably in association with a "hanger" that keeps the block in position where the water can erode the block and effect release of the cleaning system. Preferably, there should not be any large areas of water soluble ingredients in the block. As discussed herein before, the desired degree of uniformity will be accompanied by a smooth appearance of the surface, and of any cross section that is cut. The blocks of the invention can be molded into numerous shapes and sizes, but it is preferable that the blocks range in weight of from about 40 to about 120 grams to provide a life of from about four weeks to about four months.

All percentages, parts, and ratios herein are "by weight" unless otherwise stated and all numbers are approximations to account for normal variations in measurements.

The invention is illustrated by the following non limiting Examples.

| Perfume Ingredients | Wt. % |
|---|---|
| PERFUME A - Citrus Floral | |
| Blooming Ingredients | |
| Phenyl Hexanol | 3 |
| Citronellol | 5 |
| Citronellyl Nitrile | 3 |
| para Cymene | 2 |
| Decyl Aldehyde | 1 |
| Dihydro Myrcenol | 15 |
| Geranyl Nitrile | 5 |
| alpha-Ionone | 2 |
| Linalyl Acetate | 5 |
| α Pinene | 3 |
| beta-Myrcene | 1.5 |
| d Limonene | 15 |
| beta-Pinene | 3 |
| Delayed Blooming Ingredients | |
| Anisic Aldehyde | 1 |
| beta gamma Hexenol | 0.3 |
| cis-3-Hexenyl Acetate | 0.2 |
| cis-Jasmone | 1 |
| Linalool | 8 |
| Nerol | 3 |
| Citral | 4 |
| 4-Terpineol | 4 |
| Other Ingredients | |
| Amyl Salicylate | 1 |
| Hexyl Cinnamic Aldehyde | 5 |
| Hexyl Salicylate | 3 |
| P. T. Bucinal | 5 |
| Patchouli alcohol | 1 |
| Total | 100 |
| PERFUME B - Rose Floral | |
| Blooming Ingredients | |
| Citronellol | 15 |
| Citronellyl Nitrile | 3 |
| Decyl Aldehyde | 1 |

-continued

| Perfume Ingredients | Wt. % |
|---|---|
| Dihydro Myrcenol | 4 |
| Dimethyl Octanol | 5 |
| Diphenyl Oxide | 1 |
| Geranyl Acetate | 3 |
| Geranyl Formate | 3 |
| alpha-Ionone | 3 |
| Isobornyl Acetate | 4 |
| Linalyl acetate | 4 |
| Citronellyl acetate | 5 |
| Delayed Blooming Ingredients | |
| Geraniol | 6 |
| Phenyl Ethyl Alcohol | 13 |
| Terpineol | 4 |
| Other Ingredients | |
| Aurantiol | 3 |
| Benzophenone | 3 |
| Hexyl Cinnamic Aldehyde | 10 |
| Lilial | 10 |
| Total | 100 |

PERFUME C - Woody Floral, Powdery

| Perfume Ingredients | Wt. % |
|---|---|
| Blooming Ingredients | |
| Carvacrol | 1 |
| Citronellol | 5 |
| Isobornyl Acetate | 8 |
| alpha ionone | 5 |
| beta-Myrcene | 1 |
| alpha-Pinene | 4 |
| beta-Pinene | 3 |
| Tetrahydro Myrcenol | 6 |
| Verdox | 2.8 |
| Vertenex | 10 |
| Allyl Ocimene | 0.3 |
| Delayed Blooming Ingredients | |
| Anisic Aldehyde | 3 |
| Camphor gum | 2 |
| Cinnamic Aldehyde | 2 |
| para-Cresyl Methyl Ether | 0.1 |
| cis-Jasmone | 0.5 |
| Veridine | 5 |
| Other Ingredients | |
| Cedrol | 3 |
| Cedryl Acetate | 2 |
| Coumarin | 6 |
| Ethyl Vanillin | 0.3 |
| Galaxolide 50% in IPM | 5 |
| Hexyl Cinnamic Aldehyde | 5 |
| Isoeugenol | 2 |
| Lilial | 8 |
| Methyl Cinnamate | 3 |
| Patchouli alcohol | 3 |
| Vetivert Acetate | 4 |
| Total | 100 |

PERFUME D - Fruity Floral

| Perfume Ingredients | Wt. % |
|---|---|
| Blooming Ingredients | |
| Allyl Heptoate | 2 |
| Citronellyl Nitrile | 3 |
| Dihydro Myrcenol | 5 |
| Limonene | 5 |
| Geranyl Nitrile | 2 |
| alpha-Ionone | 4 |
| Linalyl Acetate | 8 |
| Methyl Chavicol | 0.5 |
| d-Limonene | 15 |
| Verdox | 2 |
| Tetrahydrolinool | 5 |
| Delayed Blooming Ingredients | |
| Anisic Aldehyde | 2 |
| Ethyl Acetate | 1 |
| Ethyl Benzoate | 1 |
| Linalool | 3 |
| Methyl Anthranilate | 5 |
| Citral | 2 |
| delta Nonalactone | 1 |
| Other Ingredients | |
| Aurantiol | 2 |
| Ethylene Brassylate | 2 |
| Galaxolide 50 IPM | 10 |
| Hexyl Salicylate | 5 |
| Iso E Super | 5 |
| Phenoxy Ethyl Isobutyrate | 9.5 |
| Total | 100 |

Perfume E is especially stable for compositions with compositions which contain bleaches.

| Perfume Ingredients | Wt. % |
|---|---|
| PERFUME E - Fruity Lemon | |
| Blooming Ingredients | |
| Dihydro Myrcenol | 1 |
| Alpha Pinene | 2.5 |
| para-Cymene | 0.5 |
| Isononyl Alcohol | 0.5 |
| Tetrahydro Linalool | 45 |
| d-Limonene | 44 |
| Verdox | 1 |
| Delayed Blooming Ingredients | |
| Camphor gum | 0.5 |
| Dimethyl Benzyl Carbinol | 1 |
| Eucalyptol | 1 |
| Fenchyl Alcohol | 1.5 |
| Dimetol | 1.5 |
| Total | 100 |

PERFUME F - Citrus Lime

| Perfume Ingredients | Wt. % |
|---|---|
| Blooming Ingredients | |
| Citronellyl Nitrile | 2 |
| Decyl Aldehyde | 0.5 |
| Dihydro Myrcinol | 10 |
| Geranyl Nitrile | 3 |
| Linalyl Acetate | 5 |
| d-Limonene | 30 |
| para-Cymene | 1.5 |
| Phenyl Hexanol | 5 |
| alpha-Pinene | 2.5 |
| Terpinyl Acetate | 2 |
| Tetrahydro Linalool | 3 |
| Verdox | 1 |
| Delayed Blooming Ingredients | |
| Benzyl Propionate | 2 |
| Eucalyptol | 2 |
| Fenchyl Alcohol | 0.5 |
| Flor Acetate | 7 |
| cis-3-hexyl tiglate | 0.5 |
| Linalool | 7 |
| 4-Terpineol | 2 |
| Citral | 3 |
| Octyl aldehyde | 0.5 |
| Frutene | 5 |

| Perfume Ingredients | Wt. % |
|---|---|
| *Other Ingredients* | |
| Methyl Dihydro Jasmonate | 5 |
| Total | 100 |
| PERFUME G - Citrus Fruity Floral | |
| *Blooming Perfume Ingredients* | |
| Allyl Heptoate | 1.20 |
| Beta Pinene | 1.20 |
| Camphene | 1.20 |
| Citronellal Nitrile | 2.40 |
| Citronellol | 6.10 |
| Citronellyl Propionate | 3.00 |
| Decyl Aldehyde | 0.60 |
| Dihydro Myrcenol | 6.10 |
| Geranyl Acetate | 1.20 |
| Iso Bornyl Acetate | 3.60 |
| limonene | 3.60 |
| Linalyl Acetate | 2.40 |
| Orange Terpenes | 12.10 |
| Rhodinol 70 | 3.60 |
| Terpinyl Acetate | 2.40 |
| Tetra Hydro Linalool | 2.40 |
| Thymol NF | 1.20 |
| Verdox | 2.40 |
| *Delayed Blooming Perfume Ingredients* | |
| Allyl Caproate | 1.20 |
| Benzyl Alcohol | 2.40 |
| Citral | 2.40 |
| Flor Acetate | 2.80 |
| Frutene | 1.50 |
| Hydroxycitronellal | 6.10 |
| Methyl Anthranilate | 3.60 |
| Nerol | 6.10 |
| Phenyl Ethyl Alcohol | 12.30 |
| Terpineol | 4.90 |
| Total | 100 |

Following are nonlimiting examples of moisture-activated encapsulated perfumes, e.g., cyclodextrin/perfume inclusion complexes and matrix perfume microcapsules, that can be incorporated in the compositions of this invention.

Cyclodextrin/Perfume Complex.

A mobile slurry is prepared by mixing about 1 Kg of beta-cyclodextrin and about 1 liter of water in a stainless steel mixing bowl of a KitchenAid™ mixer using a plastic coated heavy-duty mixing blade. Mixing is continued while about 175 g of the perfume is slowly added. The liquid-like slurry immediately starts to thicken and becomes a creamy paste. Stirring is continued for about 30 minutes. About 0.5 liter of water is then added to the paste and blended well. Stirring is resumed for about an additional 30 minutes. During this time the complex again thickens, although not to the same degree as before the additional water is added. The resulting creamy complex is spread in a thin layer on a tray and allowed to air dry. This produces about 1.1 Kg of granular solid which is ground to a fine powder. Cyclodextrin/perfume complexes are highly preferred as moisture activated encapsulated perfumes because they remain intact without perfume release/loss in the milling and/or tableting process to make the toilet bowl detergent blocks.

Matrix Perfume Microcapsules.

An example of water-activated matrix perfume microcapsules is made according to Example 1 of U.S. Pat. No. 3,971,852, except that 60 parts of blooming perfume composition is used instead of 120 parts of orange oil. Lower perfume loading levels, preferably about 40% or less, more preferably about 30% or less of the maximum disclosed in U.S. Pat. No. 3,971,852, is used to minimize the crushing and cracking of the capsules in the milling and/or tableting process to make the toilet bowl detergent blocks.

EXAMPLE I

Toilet Rim-Block Compositions

| EXAMPLE Component | 1 Wt. % | 2 Wt. % | 3 Wt. % | 4 Wt. % |
|---|---|---|---|---|
| Cocoamidopropylbetaine* | 21 | 25 | 17 | 25 |
| Sodium Citrate | 25 | 30 | 20 | 32 |
| Perfume A | 6 | — | — | — |
| Perfume B | — | 5 | — | — |
| Perfume C | — | — | 7 | — |
| Perfume D | — | — | — | 5 |
| Polyethylene Glycol (MW-8000) | 25 | 32 | 20 | 20 |
| Hydroxyethylcellulose (VG-40) | — | 5 | — | — |
| Hydroxyethylcellulose (VG-30,000) | 20 | — | 35 | — |
| Hydroxyethylcellulose (VG-100,00) | — | — | — | 15 |
| Blue Dye (0.45% solution) | 1 | 0 | 0 | — |
| Soft Water | 2 | 3 | 1 | 3 |
| Total | 100 | 100 | 100 | 100 |

EXAMPLE II

Toilet Rim-Block Compositions

| EXAMPLE Component | 1 Wt. % | 2 Wt. % | 3 Wt. % | 4 Wt. % |
|---|---|---|---|---|
| Cocoamidopropylbetaine* | 21 | 25 | 17 | 25 |
| Sodium Citrate | 23 | 27 | 20 | 30 |
| β Cyclodextrin/Perfume E complex powder | 10 | — | — | — |
| β Cyclodextrin/Perfume F complex powder | — | 10 | — | — |
| Matrix microcapsules with Perfume C | — | — | 8 | — |
| Matrix microcapsules with Perfume D | — | — | — | 7 |
| Polyethylene Glycol (MW-8000) | 23 | 30 | 20 | 20 |
| Hydroxyethylcellulose (VG-40) | — | 5 | — | — |
| Hydroxyethylcellulose (VG-30,000) | 20 | — | 35 | — |
| Hydroxyethylcellulose (VG-100,00) | — | — | — | 15 |
| Blue Dye (0.45% solution) | 1 | 0 | 0 | — |
| Soft Water | 2 | 3 | 1 | 3 |
| Total | 100 | 100 | 100 | 100 |

EXAMPLE III

Toilet In-Tank Block Compositions

| EXAMPLE Component | 1 Wt. % | 2 Wt. % | 3 Wt. % | 4 Wt. % |
|---|---|---|---|---|
| Cocoamidopropylbetaine* | 29 | 26 | 23 | 24 |
| Sodium Citrate | 27 | 27 | 27 | 27 |
| Perfume A | 1 | — | — | — |
| Perfume B | — | 1 | — | — |
| Perfume C | — | — | 1 | — |
| Perfume D | — | — | — | 1 |
| Hydroxyethylcellulose (Hercules Natrosol 250-HHX) | 9 | 18 | 27 | 27 |
| Polyox WSR ® Coagulant (Union Carbide) | 27 | 18 | 9 | 9 |
| Blue Dye (0.45% solution) | 1 | 1 | 1 | 1 |
| Soft Water | 6 | 9 | 12 | 9 |
| Total | 100 | 100 | 100 | 100 |

EXAMPLE IV

Toilet In-Tank Block Compositions

| EXAMPLE<br>Component | 1<br>Wt. % | 2<br>Wt. % | 3<br>Wt. % | 4<br>Wt. % |
|---|---|---|---|---|
| Cocoamidopropylbetaine* | 27 | 25 | 23 | 24 |
| Sodium Citrate | 26 | 26 | 26 | 26 |
| β Cyclodextrin/Perfume A complex powder | 5 | — | — | — |
| β Cyclodextrin/Perfume E complex powder | — | 5 | — | — |
| Matrix microcapsules with Perfume B | — | — | 3 | — |
| Matrix microcapsules with Perfume F | — | — | — | 3 |
| Hydroxyethylcellulose (Hercules Natrosol 250-HHX) | 9 | 17 | 26 | 26 |
| Polyox WSR ® Coagulant (Union Carbide) | 26 | 17 | 9 | 9 |
| Blue Dye (0.45% solution) | 1 | 1 | 1 | 1 |
| Soft Water | 6 | 9 | 12 | 9 |
| Total | 100 | 100 | 100 | 100 |

*$C_{12-16}$ fatty acylamidopropylbetaine from Goldschmidt (Tego Betaine D).

What is claimed is:

1. A block detergent composition for keeping a toilet bowl clean comprising:
   (1) from about 0.1% to about 10% of a blooming perfume composition comprising blooming perfume ingredients selected from the group consisting of: ingredients having a boiling point of less than about 260° C. and a ClogP of at least about 3, and wherein said perfume composition comprises at least 5 different blooming perfume ingredients;
   (2) a cleaning system comprising: detergent surfactant and detergent builder, the ratio of said detergent surfactant to said detergent builder being from about 1:100 to about 100:1; and
   (3) system for providing a concentration of from about 1 ppm to about 1000 ppm of said detergent surfactant and said detergent builder in the water of said toilet bowl, said water in said toilet bowl having a pH of from about 2 to about 11;
wherein at least a portion of said blooming perfume composition is present in moisture-activated encapsulated perfume particles selected from the group consisting of cyclodextrin/perfume inclusion complexes and water soluble matrix perfume microcapsules.

2. The composition of claim 1 wherein said blooming perfume composition also includes delayed blooming perfume ingredients selected from the group consisting of perfume ingredients having a boiling point of less than about 260° C. and a ClogP of less than about 3, wherein the ratio of blooming perfume ingredients to delayed blooming ingredients is at least 1:1.

3. The composition of claim 2 wherein said blooming perfume composition comprises at least about 50% of blooming perfume ingredients.

4. The composition of claim 2 wherein said blooming perfume composition comprises at least about 20% of blooming perfume ingredients.

5. The composition of claim 3 wherein said blooming perfume composition does not contain any single ingredient at a level of more than about 60% by weight of the perfume composition.

6. The composition of claim 6 wherein the blooming perfume ingredients are selected from the group consisting of: Allo-Ocimene, allyl cyclohexanepropionate, Allyl Heptoate, trans Anethol, Benzyl Butyrate, Camphene, Cadinene, Carvacrol, cis-3-Hexenyl Tiglate, Citronellol, Citronellyl Acetate, Citronellyl Nitrile, Citronellyl Propionate, Cyclohexyl Ethyl Acetate, Decyl Aldehyde, Dihydromycernol, Dihydromyrcenyl Acetate, 3,7 dimethyl-1-Octanol, Diphenyl Oxide, Fenchyl Acetate, Geranyl Acetate, Geranyl Formate, Geranyl Nitrile, cis-3-Hexenyl Isobutyrate, Hexyl Neopentanoate, Hexyl Tiglate, alpha-Ionone, Isobornyl Acetate, Isobutyl Benzoate, Isononyl Acetate, Isononyl Alcohol, Isopulegyl acetate lauraldehyde, d-Limonene, Linalyl Acetate, (−)-L-Menthyl Acetate, Methyl Chavicol, Methyl-n-Nonyl Acetaldehyde, Methyl Octyl Acetaldehyde, beta-Myrcene, Neryl Acetate, Nonyl Acetate, Nonyl Aldehyde, para-Cymene, alpha-Pinene, beta-Pinene, alpha-Terpinene, gamma-Terpinene, alpha-Terpinyl acetate, Tetrahydro Linalool, Tetrahydro Myrcenol, 2-Undecenal, Veratrol, Verdox, and Vertenex.

7. The composition of claim 6 wherein the delayed blooming perfume ingredients are selected from the group consisting of: Allyl Caproate, Amyl Acetate, Amyl Propionate, p-anisaldehyde, Anisole, Benzaldehyde, Benzyl Acetate, Benzyl Acetone, Benzyl Alcohol, Benzyl Formate, Benzyl Iso Valerate, Benzyl Propionate, Beta Gamma Hexenol, (+)-Camphor, (+)-Carvone, L-Carvone, Cinnamic Alcohol, Cinnamyl Formate, cis-Jasmone, cis-3-Hexenyl Acetate, Citral, Cumic alcohol, Cuminic aldehyde, Cyclal, Dimethyl Benzyl Carbinol, Dimethyl Benzyl Carbinyl Acetate, Ethyl Acetate, Ethyl acetoacetate, Ethyl Amyl Ketone, Ethyl Benzoate, Ethyl butanoate, Ethyl Hexyl Ketone, Ethyl Phenyl Acetate, Eucalyptol, Eugenol, Fenchyl Alcohol, Flor Acetate, Frutene, gamma Nonalactone, trans-Geraniol, cis-3-Hexen-1-ol, Hexyl Acetate, Hexyl Formate, Hydratropic Alcohol, Hydroxycitronellal, Indole, Isoamyl Alcohol, Isopulegol, isopropylphenylacetate, Isoquinoline, Ligustral, Linalool, Linalool Oxide, Linalyl Formate, Menthone, 4-Methyl Acetophenone, Methyl Pentyl Ketone, Methyl Anthranilate, Methyl Benzoate, Methyl Phenyl Carbinyl Acetate, Methyl Eugenol, Methyl Heptenone, Methyl Heptine Carbonate, Methyl Heptyl Ketone, Methyl Hexyl Ketone, Methyl Salicylate, Dimethyl Anthranilate, Nerol, gamma-Octalactone, 2-Octanol, Octyl Aldehyde, para-Cresol, para-Cresyl Methyl Ether, Acetanisole, 2-Phenoxy Ethanol, Phenyl Acetaldehyde, 2-Phenyl Ethyl Acetate, Phenyl Ethyl Alcohol, Phenyl Ethyl Dimethyl Carbinol, Prenyl Acetate, Propyl Butanoate, (+)-Pulegone, Rose Oxide, Safrole, 4-Terpinenol, Terpolene, Veratrole, and Veridine.

8. The composition of claim 7 wherein said detergent surfactant is an amphoteric surfactant and said detergent builder is a polycarboxylate chelating agent.

9. The composition of claim 8 wherein said detergent surfactant has the formula:

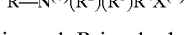

$$R-N^{(+)}(R^2)(R^3)R^4X^{(-)}$$

wherein each R is a hydrophobic group; $R^2$ and $R^3$ are each $C_{1-4}$ alkyl, hydroxy alkyl or other substituted alkyl group which can also be joined to form ring structures with the N; $R^4$ is a moiety joining the cationic nitrogen atom to the hydrophilic group X.

10. The composition of claim 9 wherein R contains from about 8 to about 22 carbon atoms and can contain unsaturation and/or linking groups selected from the group consisting of: aryl groups, amido groups, ester groups, and mixtures thereof; $R^4$ is a moiety selected from the group consisting of: an alkylene, hydroxyalkylene, or polyalkoxy group containing from about one to about four carbon atoms; and each X is a carboxylate or sulfonate group.

11. The composition of claim 8 wherein said detergent surfactant has the formula:

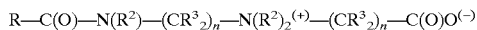

wherein each R is a hydrocarbon group containing from about 8 up to about 20 carbon atoms, each ($R^2$) is either hydrogen when ($R^2$) is attached to the amido nitrogen, or short chain alkyl or substituted alkyl containing from one to about four carbon atoms, each ($R^3$) is selected from the group consisting of hydrogen and hydroxy groups, and each n is a number from 1 to about 4, with no more than about one hydroxy group in any ($CR^3{}_2$) moiety.

12. The composition of claim 1 wherein the blooming perfume composition has at least 55% of blooming perfume ingredients.

13. The composition of claim 12 wherein the blooming perfume composition has at least 60% of blooming perfume ingredients.

14. The composition of claim 13 wherein the blooming perfume composition has at least 70% of blooming perfume ingredients.

15. The composition of claim 8 wherein said polycarboxylic chelating agent is selected from the group consisting of: citric acid; succinic acid, glutaric acid, adipic acid, maleic acid; mixtures thereof, or salt thereof.

16. The composition of claim 15 further comprising a dissolution retarding system which comprises a mixture of (1) cellulosic material that is either, hydroxypropyl cellulose or hydroxyethyl cellulose, and (2) polyethylene glycol or poly(ethylene oxide), or a polymer that contains a major percentage of polyethylene glycol or poly(ethylene oxide), so that the polymer has the characteristics of polyethylene glycol or poly(ethylene oxide), said mixture being at a level of from about 5% to about 60% by weight of said composition.

17. An article of commerce comprising a hanger for a rim-block detergent block composition containing the composition of claim 1.

18. An article of commerce comprising a hanger for a rim-block detergent block composition containing the composition of claim 16.

* * * * *